United States Patent [19]

Walker

[11] 4,207,317

[45] Jun. 10, 1980

[54] 1-ARYL-4-CARBAMOYL-PYRAZOLIN-5-ONES

[75] Inventor: Gordon N. Walker, Morristown, N.J.

[73] Assignee: Ciba-Geigy Corporation, Ardsley, N.Y.

[21] Appl. No.: 971,478

[22] Filed: Dec. 20, 1978

Related U.S. Application Data

[63] Continuation-in-part of Ser. No. 885,722, Mar. 13, 1978, abandoned.

[51] Int. Cl.$^2$ ............... A61K 31/555; A61K 31/415; C07F 3/06; C07D 231/22
[52] U.S. Cl. .................. 424/245; 424/273 P; 548/105; 548/367
[58] Field of Search ............. 548/367; 260/299; 424/245, 273 P

[56] References Cited

U.S. PATENT DOCUMENTS

| | | | |
|---|---|---|---|
| 2,459,226 | 1/1949 | Kendall et al. | 548/367 |
| 3,760,084 | 9/1973 | Marsico, Jr. et al. | 424/273 P |
| 3,905,997 | 9/1975 | Zinnes et al. | 548/367 |
| 3,953,467 | 4/1976 | Fujimura et al. | 424/273 P X |

FOREIGN PATENT DOCUMENTS 1133383  8/1962  Fed. Rep. of Germany ........... 548/367

OTHER PUBLICATIONS

Papini et al., Gazz, Chim, Ital, 89 526–539, (1959).
Berichte 46, p.3400(1913).

*Primary Examiner*—Donald G. Daus
*Assistant Examiner*—Diana G. Rivers
*Attorney, Agent, or Firm*—Theodore O. Groeger

[57] ABSTRACT

Substituted 1-phenyl-4-phenylcarbamoyl-2-pyrazolin-5-ones, e.g. those of the formula

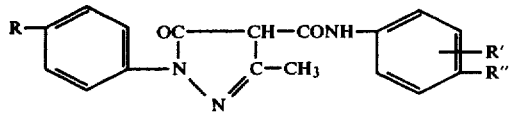

wherein each of R, R' and R" is alkyl, alkoxy, halo or trifluoromethyl, or at most 2 thereof are hydrogen; or their salts with therapeutically acceptable bases, are anti-inflammatory and anti-arthritic agents.

6 Claims, No Drawings

1-ARYL-4-CARBAMOYL-PYRAZOLIN-5-ONES

CROSS-REFERENCE TO RELATED APPLICATION

This is a continuation-in-part of application Ser. No. 885,722, filed Mar. 13, 1978 now abandoned.

BACKGROUND OF THE INVENTION

The compound of the above formula, wherein R, R' and R'' are hydrogen, is described in Gazz. Chim. Ital. 89, 533 (1959), together with its isomer of the formula

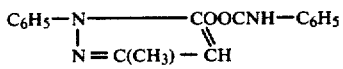

both of which are obtained from 1-phenyl-3-methyl-2-pyrazolin-5-one and phenylisocyanate, depending on the temperature at which addition is carried out, often resulting in unstable mixtures not suitable for drugs. Surprisingly, it was found that by introduction of at least one substituent R, R', R'' into said phenyl groups, and by carrying out said addition in the presence of a trialkylamine, preferably triethylamine, sufficiently pure and pharmacologically highly active substituted 1-phenyl-4-phenylcarbamoyl-2-pyrazolin-5-ones are obtained, which do not contain said unstable (phenylisocyanate-releasing) isomers [Ber. 46, 3400 (1913)].

SUMMARY OF THE INVENTION

The present invention concerns and has for its object the provision of the new substituted 1-phenyl-4-phenylcarbamoyl-2-pyrazolin-5-ones, preferably of those corresponding to Formula I

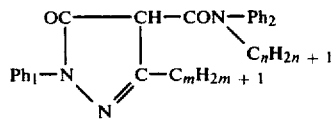

wherein each of $Ph_1$ and $Ph_2$ is phenyl or phenyl substituted by one to three identical or different members selected from lower alkyl, lower alkoxy, lower alkylthio, hydroxy, halogeno, trifluoromethyl, nitro and amino, provided that at least one of $Ph_1$ and $Ph_2$ is substituted, and each of m and n is an integer from 0 to 4; or a salt thereof derived from a pharmaceutically acceptable base; as well as of corresponding pharmaceutical compositions and of methods for the preparation and application of these products, which are useful antiinflammatory and antiarthritic agents.

DESCRIPTION OF THE PREFERRED EMBODIMENTS

Both of said phenyl groups $Ph_1$ and $Ph_2$ are preferably substituted by one or two, of the same or different members selected from the group consisting of lower alkyl, e.g. methyl, ethyl, n- or i-propyl or -butyl; lower alkoxy, e.g. methoxy, ethoxy, n- or i-propoxy or -butoxy; lower alkylthio, e.g. methylthio or ethylthio; hydroxy; halogeno, e.g. fluoro, chloro or bromo; trifluoromethyl; nitro or amino. As used above and hereinafter, the term "lower" defines such groups, or compounds respectively, containing up to 7, preferably up to 4 carbon atoms.

The lower alkyl groups $C_mH_{2m+1}$ and $C_nH_{2n+1}$ (m,n≠0) are above all methyl, but also ethyl, n- or i-propyl or -butyl. Accordingly, m is preferably 1 and n is advantageously zero.

The 5-hydroxy-tautomers of Formula I are sufficiently acidic to form salts with pharmaceutically acceptable bases, such as alkali metal or zinc hydroxides, ammonia, mono-, di- or tri-lower alkylamines or alkyleneimines, e.g. sodium, potassium, ammonium, mono-, di- or tri-(methyl or ethyl)ammonium, pyrrolidinium or morpholinium salts; or various hydrates respectively.

The compounds of the invention exhibit valuable pharmacological properties, primarily antiinflammatory activity. This can be demonstrated by in-vitro or in-vivo tests, using for the latter advantageously mammals, such as rats, guinea pigs or dogs, as test objects. The compounds of the invention can be administered to the animals either enterally, preferably orally; parenterally, e.g. subcutaneously or intravenously; or topically; for example, in the form of aqueous or oily solutions or starchy suspensions. The applied dosage may range between about 0.1 and 200 mg/kg/day, preferably between about 1 and 100 mg/kg/day, advantageously between about 5 and 50 mg/kg/day. The tests chosen are among the classical assay methods for said activity, such as the carrageenin paw-edma, or adjuvant arthritis test in rats, the canine synovitis or ultraviolet erythema assays, or more recent tests, such as neutral protease inhibition, described in Arthritis Rheum. 17, 47 (1974), or inhibition of leukocyte chemotaxis, described in Ann. N.Y. Acad. Sci., 256, 177 (1975); or decrease of neutrophil adherance, described in Amer. J. Med. 61, 597 (1976); or inhibition of prostaglandin synthetase, described in Biochem. 10, 2372 (1971).

Thus, for example, the 1-(p-methoxyphenyl)-3-methyl-4-(p-fluoro-phenylcarbamoyl)-2-pyrazolin-5-one, a representative member of the compounds of Formula I, or said salts thereof, are highly active in rats at p.o. doses as low as 5 mg/kg/day in the adjuvant arthritis assay. Accordingly, the compounds of the invention are useful antiinflammatory agents, for example, in the treatment or management of arthritic and dermatopathologic conditions.

Particularly useful are compounds of Formula I, wherein each of $Ph_1$ and $Ph_2$ is phenyl or phenyl substituted by one or two of the same or different members selected from lower alkyl, lower alkoxy, halogeno and trifluoromethyl, provided that at least one of $Ph_1$ and $Ph_2$ is substituted, and each of m and n is an integer from 0 to 2; or a salt thereof from a therapeutically acceptable base.

Another useful group comprises compounds of Formula I, wherein both $Ph_1$ and $Ph_2$ are phenyl substituted by one or two of the same or different members selected from lower alkyl, lower alkoxy, halogeno and trifluoromethyl, and each of m and n is an integer from 0 to 2; or a salt thereof from a therapeutically acceptable base.

Preferred compounds of the invention are those of Formula II

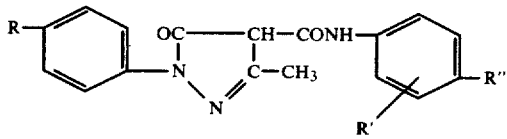

wherein each of R, R' and R" is alkyl or alkoxy with up to 4 carbon atoms; fluoro, chloro, bromo or trifluoromethyl; or at most two of R, R' and R" are hydrogen; or alkali metal, zinc or tri-lower alkylammonium salts thereof.

Outstanding are compounds of Formula II, wherein R is hydrogen and one or both of R' and R" is methyl, methoxy, fluoro, chloro or trifluoromethyl and the other is hydrogen; or the sodium, potassium, zinc or triethylammonium salt thereof.

Another group of outstanding compounds comprises those of Formula II, wherein R is methoxy, fluoro, chloro or trifluoromethyl and each of R' and R" is methyl, methoxy, fluoro, chloro or trifluoromethyl, or R' is hydrogen; or the sodium, potassium, zinc or triethylammonium salt thereof.

The compounds of the invention are prepared either according to conventional methods, for example, by:

(a) adding phenylisocyanates Ph$_2$—N=CO to compounds of Formula III

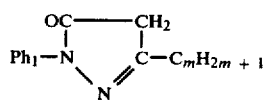

(b) condensing compounds of the Formulas IV and V

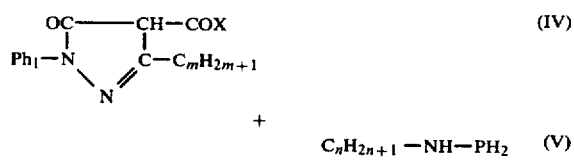

wherein X is lower alkoxy, alkanolyoxy, or halo or (c) according to the new method wherein a solution of a trialkylammonium salt of the compounds of Formula III in an aromatic hydrocarbon is treated with the phenylisocyanate Ph$_2$—N=CO and, if desired, converting any resulting product into another compound of the invention.

The addition of the isocyanate according to item (a) is preferably carried out according to said Gazz. Chim. Ital. 89 article, or according to U.S. Pat. No. 3,905,997, i.e. in the absence or presence of an inorganic base, such as sodium hydride, and a polar solvent, such as an ether, e.g. diethyl ether or tetrahydrofuran, and/or an amide or sulfoxide, e.g. dimethylformamide or —sulfoxide; advantageously at raised temperatures, e.g. at about 150° if no base is used.

The amination according to item (b) is also carried out in the usual manner, advantageously between about room temperature and about 150°, either with equivalent amounts of the reactants, preferably when the ester is used, or with an excess of the amine, or in the presence of another base, such as a tertiary amine, e.g. a tri-lower alkylamine or pyridine, when the halide of anhydride is used, in order to neutralize the generated acid. The lower alkanol, generated in the reaction with said esters, is preferably distilled off together with diluent, such as an aromatic hydrocarbon, e.g. benzene, toluene or xylene.

The new process according to item (c) is generally performed thus: The suspension of 0.3 mole of compound III in about 100 ml of the aromatic hydrocarbon, e.g. warm benzene, is treated with about 0.35 mole of an anhydrous tri-lower alkylamine, preferably triethylamine, and, when said 2-pyrazolin-5-one is dissolved, the solution of 0.3 mole of the phenylisocyanate Ph$_2$—N=CO in about 50 ml of said hydrocarbon, or a mixture thereof with some of said polar solvents mentioned under item (a), e.g. dimethylsulfoxide, necessary for solution, is added while stirring. After standing for about 2–12 hours at room temperature, the reaction mixture is reduced in volume by evaporation without any but the mildest warming. The residue is treated with an excess of diluted aqueous acid, e.g. 0.3 N hydrochloric acid, if necessary with the aid of some lower alkanol, e.g. methanol, and the crude, crystalline products are collected. They are washed with water, dried, triturated and/or recrystallized from appropriate solvents, such as lower alkanols, alkanones, alkyl ethers and/or alkanoates, e.g. methanol, acetone, diethyl ether and/or ethyl acetate.

The compounds of Formula I, so obtained, can be converted into each other according to methods known per se. Thus, for example, resulting enols can be salified with said pharmaceutically useful bases or alkali metal hydrides, advantageously in the presence of an alcoholic solvent, such as a lower alkanol, e.g. ethanol; or an ether, e.g. tetrahydrofuran; or an amide, e.g. dimethylformamide; at moderate temperatures, e.g. below 100°. Resulting salts may be converted into the free compounds by treatment with acids as mentioned above. Also a nitro group within Ph$_1$ or Ph$_2$ can be reduced, for example, with catalytically activated hydrogen, e.g. in the presence of nickel or palladium catalysts, to yield the corresponding amino compounds.

The starting materials used are known, or if new, can be prepared according to the methods used for the known analogs or illustrated by the examples herein.

The above reactions are otherwise carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives, preferably alkali metal or trialkylammonium salts of said enols. Said isocyanates may also be formed from the corresponding acid azides, and mixed anhydrides from corresponding acids and simple alkanoic acid anhydrides. In the process of the invention those starting materials are advantageously selected, which yield the above-described preferred embodiments of the invention, especially those corresponding to Formula II.

The pharmacologically active compounds of the invention are useful in the manufacture of pharmaceutical compositions containing an effective amount thereof in conjunction or admixture with excipients suitable for either enteral, parental or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade, all parts wherever given are parts by weight, and all evaporations are carried out under reduced pressure.

EXAMPLE 1

The stirred suspension of 7 g of 1-phenyl-3-methyl-2-pyrazolin-5-one in 100 ml of benzene is solubilized with 4.5 g of triethylamine, whereupon 5.5 g of p-fluorophenylisocyanate are added, resulting in separation of an oily, lower layer of the triethylammonium salt within 10–15 minutes. After standing overnight at room temperature, the mixture is evaporated at 35° and the residue is treated with 250 ml of 0.3 N hydrochloric acid. The precipitate is collected, washed with water, dried, triturated with diethyl ether ad recrystallized from ethyl acetate to yield the 1-phenyl-3-methyl-4-(p-fluorophenylcarbamoyl)-2-pyrazolin-5-one hydrate of Formula II, with R=R'=H and R''=F, melting at 172°–179° (dec.).

The solution of 5.7 g of thereof in 100 ml of methanol is combined with 50 ml of methanolic sodium methoxide prepared from 0.4 g of sodium. The mixture is evaporated, the residue triturated with diethyl ether and reprecipitated from methanol with diethyl ether to yield the corresponding sodium salt thereof, melting between 210° and 270° with decomposition.

The solution of 1 g thereof in the minimum amount of water is gradually combined with aqueous zinc chloride until no further precipitate appears. It is collected, washed with water, dried, triturated with methanol and recrystallized from aqueous dimethylformamide to yield the corresponding zinc salt, melting at 213°–220° (dec.).

EXAMPLE 2

The stirred suspension of 4.2 g of 1-(p-chlorophenyl)-3-methyl-2-pyrazolin-5-one in 100 ml of benzene is gently warmed with 2.4 g of triethylamine until all solid is dissolved. The deep red solution is combined with 2.4 g of phenylisocyanate, and after 2 hours' standing at ambient temperature, a lower layer is present. The mixture is evaporated, the residue taken up in 0.3 N hydrochloric acid and the mixture extracted with ethyl acetate. The extract is washed with water, dried, evaporated, the residue is triturated with diethyl ether and recrystallized from methanol to yield the 1-(p-chlorophenyl)-3-methyl-4-phenylcarbamoyl-2-pyrazolin-5-one of Formula II with R'=R''=H and R=Cl, melting at 212°–215° (dec.).

EXAMPLE 3

The solution of 13 g of 1-phenyl-3-methyl-2-pyrazolin-5-one in 150 ml of benzene and 9.1 g of triethylamine is combined at ambient temperature with the solution of 14.0 g of 3,4-dichlorophenylisocyanate in the minimum amount of benzene. The triethylammonium salt separates after 2 hours standing at room temperature and the mixture is evaporated. The residue is poured into 0.3 N hydrochloric acid, the solid collected, washed with water, dried, triturated with cold methanol and recrystallized from ethyl acetate to yield the 1-phenyl-3-methyl-4-(3,4-dichlorophenylcarbamoyl)-2-pyrazolin-5-one of Formula II with R=H, R'=3—Cl and R''=Cl, melting at 228°–231° (dec.).

The solution of 4.1 g thereof in the minimum amount of methanol is combined with methanolic sodium methoxide prepared from 0.26 g of sodium. The solution is combined with diethyl ether, the precipitate collected and recrystallized from methanol-diethyl ether to yield the corresponding sodium salt hemihydrate, melting at 295°1 (dec.).

EXAMPLE 4

The solution of 4.7 g of 1-phenyl-3-methyl-2-pyrazolin-5-one in 75 ml of benzene and 3.3 g of triethylamine is combined with the solution of 5.1 g of 2,5-dichlorophenylisocyanate in 25 ml of benzene. After warming the mixture briefly on the steam cone, the resulting solution is allowed to stand for 2 hours at room temperature. It is evaporated, the residue triturated with diethyl ether and recrystallized from methanol-diethyl ether to yield the triethylammonium salt-methanolate of the 1-phenyl-3-methyl-4-(2,5-dichlorophenylcarbamoyl)-2-pyrazolin-5-one, melting at 142°–147°, resolidifying and remelting at 154°–159°.

The solution of 7 g thereof in the minimum amount of methanol is treated with 5 ml of 5 N hydrochloric acid, the precipitate collected and recrystallized from methanol to yield the corresponding free compound, melting at 208°–211°.

EXAMPLE 5

The solution of 5.4 g of 1-phenyl-3-methyl-2-pyrazolin-5-one in 100 ml of benzene and 3.8 g of triethylamine is combined with 5.3 g of 3-chloro-4-fluorophenylisocyanate. The solution forms a lower layer within 5 minutes and after stirring for 90 minutes, a salt crystallizes. It is collected, washed with benzene, dried and recrystallized from ethyl acetate to yield the triethylammonium salt of the 1-phenyl-3-methyl-4-(3-chloro-4-fluorophenylcarbamoyl)-2-pyrazolin-5-one, melting at 145°–152°.

The solution of 8 g thereof in the minimum amount of aqueous methanol is treated with 10 ml of 5 N hydrochloric acid, the precipitate collected and recrystallized from methanol to yield the hemihydrate of the corresponding free compound of Formula II with R=H, R'=3—Cl and R"=F, melting at 211°–216°.

EXAMPLE 6

The solution of 4.1 g of 1-(p-methoxyphenyl)-3-methyl-2-pyrazolin-5-one in 75 ml of benzene and 2.5 g of triethylamine is combined with 2.75 g of p-fluorophenylisocyanate while stirring at ambient temperature. After standing overnight, the mixture is evaporated, the residue taken up in 0.3 N hydrochloric acid, the resulting crystals collected, washed with water, dried, triturated with ethyl acetate and recrystallized from methanol to yield the 1-(p-methoxyphenyl)-3-methyl-4-(p-fluorophenylcarbamoyl)-2-pyrazolin-5-one of Formula II with R=OCH$_3$, R'=H and R"=F, melting at 254°–256° (dec.).

EXAMPLE 7

The mixture of 0.6 g of 1-(3,4-dichlorophenyl)-3-methyl-4-carbethoxy-2-pyrazolin-5-one, 0.31 g of 3,4-dichloroaniline and 40 ml of xylene is distilled for a few minutes, refluxed 20 minutes and distilled again a few minutes. The cooled solution deposits crystals, which are collected, washed with benzene and recrystallized from ethyl acetate to yield the 1-(3,4-dichlorophenyl)-3-methyl-4-(3,4-dichlorophenylcarbamoyl)-2-pyrazolin-5-one, melting at 255°–257° (dec.).

The starting material is prepared as follows: The mixture of 1.3 g of diethyl α-acetyl-malonate, 1.3 g of 3,4-dichlorophenylhydrazine hydrochloride, 0.5 g of sodium acetate, 30 ml of ethanol and 10 ml of water is warmed on the steam cone for 10 minutes. It is diluted with water, extracted with diethyl ether, the extract washed with water, dried and evaporated. The residue is taken up in 50 ml of xylene, the solution distilled for 10 minutes and refluxed for 85 minutes. It is evaporated and the residue triturated with diethyl ether to yield the 1-(3,4-dichlorophenyl)-3-methyl-4-carbethoxy-2-pyrazolin-5-one, melting at 147°–148°.

EXAMPLE 8

1.9 g of 1-phenyl-3-methyl-4-(p-fluorophenylcarbamoyl)-2-pyrazolin-5-one hydrate (Ex. 1) are dissolved in 20 ml of acetyl chloride and the mixture warmed on the steam cone until a new precipitate appears. It is collected after cooling, washed with diethyl ether and recrystallized from ethyl acetate-diethyl ether-petroleum ether, to yield the anhydrous form of said compound of Formula II with R=R'=H and R"=F, melting at 183°–185°.

EXAMPLE 9

The stirred solution of 4.1 g of 1-(p-methoxyphenyl)-3-methyl-2-pyrazolin-5-one in 75 ml of warm benzene and 2.4 g of triethylamine is combined with the solution of 3.8 g of 3,4-dichlorophenylisocyanate in 50 ml of benzene. After standing at ambient temperature for 4 hours, the benzene is evaporated, the residue taken up in methanol and the solution poured into 100 ml of 0.3 N hydrochloric acid. The mixture is allowed to stand overnight at room temperature, the precipitate is collected, washed with water, dried, triturated with benzene-ethyl acetate and recrystallized from methanol to yield the 1-(p-methoxyphenyl)-3-methyl-4-(3,4-dichlorophenylcarbamoyl)-2-pyrazolin-5-one of Formula II with R=OCH$_3$, R'=3—Cl and R"=Cl, melting at 120°–125°, resolidifying and remelting at 228°–232° (dec.).

Analogously, the 1-(p-methoxyphenyl)-3-methyl-4-phenylcarbamoyl-2-pyrazolin-5-one is obtained, melting at 244°–246°.

EXAMPLE 10

The solution of 4.6 g of 1-phenyl-4-carbethoxy-2-pyraxolin-5-one and 2.5 g of p-fluoroaniline in 250 ml of xylene is refluxed for 100 minutes and slowly distilled for 15 minutes. The mixture is evaporated, the residue triturated with diethyl ether and recrystallized from methanol to yield the 1-phenyl-4-(p-fluorophenylcarbamoyl)-2-pyrazolin-5-one, melting at 241°–242° (dec.).

Analogously, the 1-phenyl-4-(3,4-dichlorophenylcarbamoyl)-2-pyrazolin-5-one is obtained, melting at 272°–275°.

EXAMPLE 11

The mixture of 4.2 g of 1-phenyl-4-carbethoxy-2-pyrazolin-5-one, 3.2 g of 2,4-dichloroaniline and 250 ml of xylene is distilled until 15 ml of distillate are collected.

It is refluxed for 2 hours, again distilled until 40 ml of distillate are collected and evaporated under reduced pressure. The residue is triturated with benzene, dissolved in ethyl acetate-acetone, the solution filtered, the filtrate evaporated, the residue triturated with diethyl ether and recrystallized from methanol to yield the 1-phenyl-4-(2,4-dichlorophenylcarbamoyl)-2-pyrazolin-5-one, melting at 215°–216°.

EXAMPLE 12

The solution of 2.2 g of 1-phenyl-3-methyl-4-carbethoxy-2-pyrazolin-5-one and 1.1 g of p-aminophenol in 120 ml xylene is refluxed for one hour, and 15 ml of the solvent are distilled off gradually to remove water. The cooled mixture is filtered and evaporated, the residue crystallized from warm methanol and recrystallized from ethyl acetate, to yield the 1-phenyl-3-methyl-4-(p-hydroxyphenylcarbamoyl)-2-pyrazolin-5-one melting at 135°–140° and remelting at 225°; it contains half a mole of ethyl acetate as solvate.

EXAMPLE 13

The mixture of 2.6 g of 1-phenyl-3-methyl-2-pyrazolin-5-one, 75 ml of benzene, 1.8 g of triethylamine and 2.5 g of p-methylthiophenylisocyanate is stirred at ambient temperature and allowed to stand overnight. It is evaporated; the residue taken up in methanol, the solution is filtered and combined with the mixture of 10 ml of 5 N hydrochloric acid and 250 ml of water. The precipitate formed is collected, washed with water, dried, triturated with diethyl ether and dissolved in 2 N aqueous sodium hydroxide. The solution is filtered, acidified with 5 N hydrochloric acid, the precipitate washed with water, dried, triturated with methanol and recrystallized from ethyl acetate, to yield the 1-phenyl-3-methyl-4-(p-methylthiophenylcarbamoyl)-2-pyrazolin-5-one melting at 196°–199°.

Analogously its m-methylthio-isomer is obtained, melting at 172°–174°.

EXAMPLE 14

The suspension of 3.0 g of 1-phenyl-3-methyl-2-pyrazolin-5-one in 60 ml benzene is treated with 2.0 g of triethylamine, warmed until dissolution and combined with 2.8 g of p-nitrophenylisocyanate in 30 ml of benzene while stirring. After standing for several hours at room temperature, it is filtered and the residue washed with benzene to yield the 1-phenyl-3-methyl-4-(p-nitrophenylcarbamoyl)-2-pyrazolin-5-one triethylammonium salt melting at 185°–192°.

The solution of 3.5 g thereof in 200 ml of 95% aqueous ethanol and 1 ml of triethylamine is shaken in the presence of 1.2 g of 10% palladium on charcoal at 3.1 atm. of hydrogen until 3 molar equivalents thereof have been absorbed. The mixture is filtered, evaporated and an aqueous solution of the residue neutralized with acetic acid. The precipitate is collected, washed with water, dried and recrystallized from methanol, to yield the 1-phenyl-3-methyl-4-(p-aminophenylcarbamoyl)-2-pyrazolin-5-one melting at 153°–156°.

EXAMPLE 15

The suspension of 3.1 g of 1-(p-chlorophenyl)-3-methyl-2-pyrazolin-5-one in 100 ml of benzene is treated with 1.8 g of triethylamine, warmed until dissolution and combined with 2.1 g of p-fluorophenylisocyanate while stirring. After standing overnight at room temperature it is evaporated, the residue taken up in methanol and the solution treated with the mixture of 10 ml of 5 N hydrochloric acid and 250 ml of water. The mixture is extracted with ethyl acetate, the extract washed with water, dried and evaporated. The crude solid is dissolved in 2 N aqueous sodium hydroxide, the solution filtered and acidified with 5 N hydrochloric acid. The precipitate is collected, washed with water and recrystallized from ethyl acetate-petroleum ether, to yield the 1-(p-chlorophenyl)-3-methyl-4-(p-fluorophenylcarbamoyl)-2-pyrazolin-5-one melting at 240°–242° with decomposition.

Analogously the 1-(p-methoxyphenyl)-3-methyl-4-(3-chloro-4-fluorophenylcarbamoyl)-2-pyrazolin-5-one hemihydrate is obtained, melting at 109°–113° (from chloroform).

EXAMPLE 16

According to the new process mentioned under item (c), the following compounds of Formula I are prepared from equivalent amounts of the corresponding starting materials:

| $Ph_1$ = phenyl, m = 1, n = 0, me = methyl, et = ethyl, DMF = dimethylformamide | | | | |
|---|---|---|---|---|
| No. | $Ph_2$ | Derivative | Recryst. from | m.p. °C. |
| 1 | p-$CH_3$—$C_6H_4$ | — | et acetate | 217–221 |
| 2 | p-$CH_3O$—$C_6H_4$ | — | " | 170–176 |
| 3 | m-$CH_3O$—$C_6H_4$ | — | meOH | 204–207 |
| 4 | o-$CH_3O$—$C_6H_4$ | — | " | 203–208 |
| 5 | m-F—$C_6H_4$ | $H_2O$ | et acetate | 141–144(dec.) |
| 6 | o-F—$C_6H_4$ | — | " | 140–143(dec.) |
| 7 | p-Cl—$C_6H_4$ | ½ $H_2O$ | meOH | 220–225(dec.) |
| 8 | m-Cl—$C_6H_4$ | $H_2O$ | et acetate | 123–133(dec.) |
| 9 | o-Cl—$C_6H_4$ | — | meOH | 242–245(dec.) |
| 10 | p-Br—$C_6H_4$ | — | meOH + etOH | 234–236(dec.) |
| 11 | m-$CF_3$—$C_6H_4$ | ½ $H_2O$ | etOH + $H_2O$ | 163–167(dec.) |
| 12 | p-$NO_2$—$C_6H_4$ | — | meOH + DMF | 268–270(dec.) |
| 13 | 3,4-$(CH_3)_2$—$C_6H_3$ | — | acetone | 205–213 |
| 14 | 3-Cl-4-$CH_3$—$C_6H_3$ | $H_2O$ | " | 145–150(dec.) |
| 15 | 2,4-$F_2$—$C_6H_3$ | — | meOH + $H_2O$ | 185–187 |
| 16 | 2,3-$Cl_2$—$C_6H_3$ | — | " | 258–260 |
| 17 | 2,4-$Cl_2$—$C_6H_3$ | — | $(meO)_2C_2H_4$ | 245–247(dec.) |
| 18 | 2,6-$Cl_2$—$C_6H_3$ | — | meOH | 233–238(dec.) |
| 19 | 3,5-$Cl_2$—$C_6H_3$ | meOH | " | 103–106(dec.) |
| 20 | 3-$CF_3$-4-Cl—$C_6H_3$ | — | " | 225–229 |
| 21 | 3-$NO_2$-4-Cl—$C_6H_3$ | — | " | 242–247(dec.) |
| 22 | 2,4-$Br_2$—$C_6H_3$ | — | etOH | 242–248(dec.) |
| 23 | 2,4,5-$Cl_3$—$C_6H_2$ | — | " | 247–250 |

EXAMPLE 17

The solution of 1.3 g of 1-phenyl-3-methyl-4-carbethoxy-2-pyrazolin-5-one and 0.7 g of p-fluoroaniline in 50 ml of xylene is distilled until 5 ml distillate are collected, refluxed for 2 hours and evaporated. The residue is triturated with diethyl ether and dried, to yield the 1-phenyl-3-methyl-4-(p-fluorophenylcarbamoyl)-2-pyrazolin-5-one, melting at 182°–184°; it is identical with that obtained according to Example 8.

EXAMPLE 18

Preparation of 10,000 tablets each containing 100.0 mg of the active ingredient:

Formula:

| | |
|---|---|
| 1-(p-methoxyphenyl)-3-methyl-4-(p-fluorophenylcarbamoyl)-2-pyrazolin-5-one | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Analogously tablets are prepared, containing one of the other compounds illustrated by the previous examples.

EXAMPLE 19

Preparation of 1000 capsules each containing 25 mg of the active ingredient.

Formula:

| | |
|---|---|
| 1-(p-methoxyphenyl)-3-methyl-4-(p-fluorophenylcarbamoyl)-2-pyrazolin-5-one | 25.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 315 mg of said mixture each, using a capsule filling machine.

Analogously capsules are prepared, containing 25-100 mg of the other compounds disclosed and illustrated herein, especially those of Formula II, or the alkali metal, zinc or tri-lower alkylammonium salts thereof.

EXAMPLE 20

To the stirred suspension of 920 g of 1-(p-methoxyphenyl)-3-methyl-2-pyrazolin-5-one in 9,600 ml of toluene 460 g of triethylamine are added during 5 minutes, followed by 618 g of p-fluorophenylisocyanate. The mixture is stirred under nitrogen overnight at room temperature, cooled to 10° and combined with 5,000 ml of 1 N aqueous sodium hydroxide. The mixture is stirred for 15 minutes, the organic phase separated and extracted twice with 2,000 ml of 1 N aqueous sodium hydroxide again. The combined aqueous solutions are washed twice with 2,000 ml of diethyl ether each, cooled to 5° and acidified with 900 ml of concentrated hydrochloride acid during 30 minutes. The resulting suspension is stirred for 1 hour, filtered and the residue washed 6 times with 2,000 ml of water each. 1,364 g thereof are dissolved in 55,000 ml of boiling ethanol, the solution filtered hot and the filtrate stirred under nitrogen overnight at room temperature. The precipitate formed is filtered off, washed twice with 1,000 ml of cold ethanol each and recrystallized from ethanol again, to yield the 1-(p-methoxyphenyl)-3-methyl-4-(p-fluorophenylcarbamoyl)-2-pyrazolin-5-one melting at 255°-257° with decomposition; it is identical with that obtained according to Example 6.

The starting material is obtained as follows: To the suspension of 2,700 g of p-methoxyphenylhydrazine in 24,600 ml of 50% aqueous ethanol, the solution of 1,411 g of sodium acetate in 3,000 ml of water is added while stirring under nitrogen at room temperature for 15 minutes, followed by 2,148 g of ethyl acetoacetate during 30 minutes at 25°-30°. The mixture is refluxed for 45 minutes, slowly cooled to 10° and stirred overnight. The precipitate formed is filtered off, washed twice with 2,000 ml of cold 50% aqueous ethanol each, and dissolved in 2,000 ml of boiling anhydrous ethanol. The solution is stirred at room temperature overnight, the precipitate formed filtered off and washed twice with 500 ml of cold ethanol, to yield the 1-(p-methoxyphenyl)-3-methyl-2-pyrazolin-5-one melting at 125°-128°.

What is claimed is:

1. A compound and corresponding to the formula

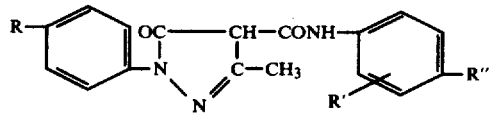

wherein each of R, R' and R" is alkyl or alkoxy with up to 4 carbon atoms; fluoro, chloro, bromo or trifluoromethyl; or R and R' are hydrogen; or an alkali metal, zinc or triethylammonium salt thereof.

2. A compound as claimed in claim 1, in which formula R is hydrogen and one or both of R' and R" is methyl, methoxy, fluoro, chloro or trifluoromethyl or R' is hydrogen; or the sodium, potassium, zinc or triethylammonium salt thereof.

3. A compound as claimed in claim 1, in which formula R is methoxy, fluoro, chloro or trifluoromethyl and each of R' and R" is methyl, methoxy, fluoro, chloro or trifluoromethyl, or R' is hydrogen; or the sodium, potassium, zinc or triethylammonium salt thereof.

4. A compound as claimed in claim 3 and being the 1-(p-methoxyphenyl)-3-methyl-4-(p-fluorophenylcarbamoyl)-2-pyrazolin-5-one, or a hydrate, the sodium, potassium, zinc or triethylammonium salt thereof.

5. An antiinflammatory or antiarthritic pharmaceutical composition comprising a correspondingly effective amount of a compound claimed in claim 1, together with a pharmaceutical excipient.

6. A method of treating inflammatory or arthritic conditions in mammals, which consists in administering to said mammals enterally, parenterally or topically a composition as claimed in claim 5.

* * * * *